United States Patent [19]

Laine et al.

[11] Patent Number: 5,587,292
[45] Date of Patent: Dec. 24, 1996

[54] DIAGNOSIS OF FUNGAL INFECTIONS WITH A CHITINASE

[75] Inventors: Roger A. Laine; Wai C. J. Lo, both of Baton Rouge, La.

[73] Assignee: Board of Supervisors of Louisiana State University and Agricultural and Mechanical College, Baton Rouge, La.

[21] Appl. No.: 402,772

[22] Filed: Mar. 9, 1995

Related U.S. Application Data

[63] Continuation of Ser. No. 288,969, Aug. 10, 1994, abandoned, which is a continuation of Ser. No. 171,184, Dec. 21, 1993, abandoned, which is a continuation of Ser. No. 827,722, Jan. 29, 1992, abandoned, which is a continuation-in-part of Ser. No. 620,909, Dec. 3, 1990, abandoned, which is a continuation of Ser. No. 53,029, May 22, 1987, abandoned.

[51] Int. Cl.$^6$ .................... G01N 33/53; G01N 33/532; G01N 33/536; G01N 33/569
[52] U.S. Cl. .................. 435/7.9; 435/4; 435/7.1; 435/7.94; 435/18; 435/30; 435/34; 435/201; 435/960; 436/800; 436/801; 436/804; 436/805
[58] Field of Search ................... 435/7.21, 7.31, 435/172.3, 206, 7.9, 4, 7.1, 18, 30, 34, 201, 900, 7.94; 424/93.1, 93.2, 93.21; 436/800, 801, 804, 805

[56] References Cited

U.S. PATENT DOCUMENTS

| | | | |
|---|---|---|---|
| 3,862,007 | 1/1975 | Smirnoff et al. | 435/206 |
| 5,004,699 | 4/1991 | Winters et al. | 435/7.31 |
| 5,352,607 | 10/1994 | Laine et al. | 435/252.33 |

OTHER PUBLICATIONS

ATCC (1985) In Catalog of Bacteria, Phages and rRNA vectors p. 213.
Davis et al. (1980) in Microbiology, 3rd Ed. Harper, Row, N.Y. pp. 818–820.
Voller et al. (1976.) in Manual of Clinical Immunology. Rose et al., Eds. American Soc. Microbiol. pp. 506–512.
Collaborative Research Inc. Catalog (1989) p. 28.
Ohtakara et al. 1979. J. Ferment. Technology 57(3):169–177. Abstract Only.
Chamberland, et al, "Chitinase–Gold Complex Used to Localized Chitin Ultrastructurally in Tomato Root Cells," Histochem. J., vol. 17, pp. 313–321.
Ou, et al, "Isolation, Characterization and Molecular Cloning of an Endo–Chitinase from Vibrio parahemolyticus," Louisiana State University draft manuscript (1991).
Lo, et al, "DNA Sequence and High Expression Level for an Endo–Chitinase from Vibrio parahemolyticus," Louisana State University draft manuscript (1991)..
Benhamou, et al, "Attempted Localization of a Substrate for Chitinases in Plant Cells Reveals Abundant N–acetyl–D–glucosamine Residues in Secondary Walls," Biology of the Cell, vol. 67, No. 3, pp. 341–350 (1989).

M. A. Benjaminson, "Conjugates of Chitinase with Fluorescein Isothiocyanate or Lissamine Rhodamine as Specific Stains for Chitin In Situ," Stain Technology, vol. 44, pp. 27–31 (1969).
M. A. Benjaminson et al.,"Ferritin–Labelled Enzyme: a Tool or Electron Microscopy," Nature, vol. 210, pp. 1275–1276 (1966).
R. P. Haugland, "Molecular Probes Handbook of Fluorescent Probes and Research Chemicals" (1992).
M. Meyberg, "Selective Staining of Fungal Hyphae in Parasitic and Symbiotic Plant–Fungus Associations," Histochemistry, vol. 88, pp. 197–199 (1988).
G. Marquis et al., "Histochemical and Immunochemical Study of the Fate of Candida albicans inside Human Neutrophil Phagolysosomes," J. Leukocyte Biol., vol. 50, pp. 587–599 (1991).
M. E. Young, et al., "Kinetics of Chitinase Production. I. Chitin Hydrolysis," Biotech. and Bioeng., vol. 27, pp. 769–775 (1985).
C. Jeuniaux, "Recherches Sur Les Chitinases, II.–Purification de la Chitinase d'un Streptomycète, et Séparation Électrophorétique de Principes Chitinolytiques Distincts," Arch. Int. Physiol. Biochem., vol. 67, pp. 597–617 (1959).
Y. Tominaga et al., "Purification and Some Properties of Two Chitinases from Streptomyces orientalis which Lyse Rhizopus Cell Wall," Agr. Biol. Chem., vol. 40, pp. 2325–2333 (1976).
A. Ohtakara et al., "Purification and Some Properties of Chitinase from Vibrio sp.," J. Ferment. Technol., vol. 57, pp. 169–177 (1979).
J. Molano et al., "A Rapid and Sensitive Assay for Chitinase Using Tritiated Chitin," Anal. Biochem., vol. 83, pp. 648–656 (1977).
R. A. Tom et al., "Effect of Reaction Conditions on Hydrolysis of Chitin by Serratia marcescens QMB1466 Chitinase," J. Food Sci., vol. 46, pp. 646–647 (1981).
A. T. Bull, "Inhibition of Polysaccharases by Melanin: Enzyme Inhibition in Relation to Mycolysis ," Arch. Biochem. Biophys., vol. 137, pp. 345–356 (1970).
M. Charpentier et al., "The Chitin–Degrading Enzyme System of a Streptomyces Species," Int. J. Biochem. vol. 15, pp. 289–292 (1983).
A. Ōtakara, "Studies on the Chitinolytic Enzymes of Black–koji Mold. Part II. Purification of Chitinase," Agr. Biol. Chem., vol. 25, pp. 54–60 (1961).
E. Danulat, "Role of bacteria with regard to chitin degradation in the digestive tract of the cod Gadus morhua," Mar. Biol., vol. 90, pp. 335–343 (1986).

*Primary Examiner*—Brian R. Stanton
*Attorney, Agent, or Firm*—John H. Runnels

[57] ABSTRACT

A novel method for detecting chitin, and for diagnosing fungal infections (including yeast infections), with a chitinase or other chitin-specific binding protein. This method should allow the convenient, broad spectrum diagnosis of fungal infections in tissue samples or in body fluids. Fungal infections are a particular problem in immunocompromised hosts such as AIDS patients, where they can cause opportunistic infections. This invention overcomes difficulties experienced by prior methods of diagnosing fungal infections.

36 Claims, No Drawings

DIAGNOSIS OF FUNGAL INFECTIONS WITH A CHITINASE

CROSS REFERENCES TO RELATED APPLICATIONS

This application is a continuation of patent application Ser. No. 08/288,969, filed Aug. 10, 1994, now abandoned; which in turn is a continuation of patent application Ser. No. 08/171,184, filed Dec. 21, 1993, now abandoned; which in turn is a continuation of patent application Ser. No. 07/827,722, filed Jan. 29, 1992, now abandoned; which in turn is a continuation-in-part of patent application Ser. No. 07/620,909, filed Dec. 3, 1990, now abandoned which in return is a continuation of patent application Ser. No. 07/053,029, filed May 22, 1987, now abandoned. The 07/620,909 application was abandoned in favor of a continuation application, Ser. No. 07/876,894, filed Apr. 29, 1992, now U.S. Pat. No. 5,352,607, issued Oct. 4, 1994. The entire disclosures of both the 07/620,909 and the 07/053,029 applications are incorporated by reference.

BACKGROUND OF THE INVENTION

This invention pertains to the diagnosis of fungal infections, particularly to the diagnosis of fungal infections with a chitinase.

Fungal infections are a major problem today, particularly in immunocompromised hosts such as acquired immune deficiency syndrome (AIDS) patients. As many as five million people worldwide are currently, believed to be infected with the human immunodeficiency virus (HIV). HIV, a retrovirus, causes AIDS. AIDS is characterized by profound derangement in cell-mediated immunity, leading to multiple opportunistic infections and unusual neoplasms.

Opportunistic diseases are the predominant causes of morbidity and mortality in AIDS patients. *Pneumocystis carinii* pneumonia (PCP) is by far the most commonly reported (56%) opportunistic infection in AIDS patients in America and Europe. *Pneumocystis carinii* has recently been reclassified as a fungus according to molecular taxonomy. Twenty-four other infections and neoplastic diseases were listed as indicators of AIDS in the 1987 revision of the Center for Disease (CDC) case definition. In the 1988 revision of the definition of AIDS by CDC and the World Health Organization (WHO), candidosis of the esophagus, trachea, bronchi, or lungs and meningeal cryptococcosis were recognized as important "indicator" diseases. In the presence of laboratory evidence of HIV infection, disseminated coccidioidomycosis and histoplasmosis are also considered indicative of AIDS. It has been estimated that 58–81% of all AIDS patients contract a fungal infection at some time during the prodromal stage or after developing AIDS, and that 10–20% have died as a direct consequence of fungal infections. Major mycoses related to AIDS include candidosis, cryptococcosis (yeasts), histoplasmosis, and coccidioidomycosis (dimorphic fungi). Deep, severe, but relatively rare mycoses related to AIDS include penicilliosis, blastomycosis, paracoccidioidomycosis, sporotdchosis, aspergillosis, mucormycosis, yeast infections, and nocardiosis.

Aspergillosis, while less common in AIDS patients, is a common fungal infection in other immunodepressed patients, occurring at a rate as high as 70% in patients with leukemia after 30 days of neutropenia. Cutaneous fungal infections related to AIDS include seborrheic dermatitis, dermatophytosis, trichosporonosis, and alternariosis.

In addition to the pathological damage resulting directly from fungal infections, fungal antigens can act as immunosuppressors which may play a role as a cofactor in the development of AIDS. While small amounts of fungal antigen can stimulate the immune response, an excess of antigen may have an adverse effect on cellular immunity. Fungal circulating antigens, such as mannan in candidosis, and glucuronoxylomannan in cryptococcosis may be present in excess in acute fungal infections. Candidal antigens may be important cofactors in AIDS. It is imperative that treatment must be undertaken rapidly and efficiently before these conditions lead to invasive forms. The immunosuppressive effect of other fungal antigens by induction of T-suppressor activity has also been proposed.

Systemic fungal infections are difficult to diagnose antemortem in AIDS patients. Unfortunately, autopsy is often the only available route to diagnose fungal infections. AIDS patients with fungal infections may have nonspecific symptoms over a long period of time. It has been difficult to establish definitive diagnoses from patients' body fluids. Histologic identification of organisms requires invasive procedures, with possible attending complications. Isolation of the organisms in blood culture, when possible, can sometimes be used for diagnosis. Even so, proper diagnosis is delayed because of the time required to process the specimens and culture the fungus. This delay alone can result in progressive deterioration from the disease. Some AIDS patients with fungal infections respond to appropriate therapy quickly with early diagnosis, although continued lifetime therapy may be necessary due to their underlying abnormal immune systems.

To improve the care of AIDS and other immunocompromised patients, a mechanism for the early diagnosis of fungal infections is imperative. Prompt implementation of an appropriate antifungal therapy provides a better environment for antiviral chemotherapy. Despite recent advances in anti-fungal therapeutics, which show promising efficacy for many of the mycoses, a rapid, sensitive, and accurate fungal diagnostic method which is also quantitative and broad-spectrum is still unavailable.

Chitin is a substance common to most fungi. Chitin is a class of polymers of N-acetyl-glucosamine. Chitin and glucan are the major constituents of cell walls of most fungi, and of some yeasts. It has been observed that the cell wall composition of a fungus is not always fixed, and may vary during the life cycle in a single species. Recent identification of chitin in certain stages in Oomycetes is an example.

Many diagnostic methods presently available for fungi are designed to detect specific anti-fungal antibodies in body fluids such as blood or serum, for example, anti-candida albicans, anti-cryptococcus, anti-histoplasma, anti-blastomyces, anti-aspergillus and anti-coccidioidomyces. These tests include immunodiffusion, latex antibody agglutination, complement fixation and candida enzyme immunoassay.

The only currently available quantitative diagnostic test for circulating fungal antigen, Cryptococcus latex agglutination, is limited to detection of Cryptococcus. For a reliable result, treatment of the sample with a protease, "Pronase," is necessary. Due to the low sensitivity of each individual test (e.g., about 80% for an immunodiffusion test), a single assay is often not definitive.

There are other available methods for the selective histologic identification of fungal organisms in tissue specimens, each of which has disadvantages. These methods generally have a broader sensitivity than antibody detection methods, in that they can recognize more than one species of fungi. Their common disadvantages are difficulties when applied to samples of body fluids, because proper sample fixation can be difficult, and their inability to give good quantitative results. Grocott methenamine silver nitrate (GMS) stain is by far the most common currently used method in the pathology laboratory. GMS staining takes advantage of the presence of polysaccharides in most fungal organisms to create a contrasting image between the fungus and the host tissue. The stain is not as effective when it is used in the cytospin or other samples of body fluids. GMS staining can be non-specific, due to its indiscriminate recognition of connective tissue polysaccharides (e.g. glycosaminoglycans, and mucin), and is not quantitative. Other histochemical stains for fungal organisms include calcofluor/cellufluor, India Ink, lectin label, and Rylus BSU. Some of the specific disadvantages of the individual methods are the following:

Calcofluor/Cellufluor

This method uses calcofluor/cellufluor to bind to the chitin of fungal organisms, which will then self-fluoresce under ultraviolet light. This method requires fluorescence microscopy, which limits its use in small clinics.

India Ink

This method uses India Ink to detect capsulated organisms such as Cryptococci, but is limited because it detects only cells with such a capsule. Many fungi do not have such a capsule.

Lectin label

Lectin label has been used in the past to stain fungi with a specific lectin-binding property (e.g., wheat germ agglutinin). However, non-specific staining is problematic.

Rylus BSU

This method stains the chitinous cell walls of fungal organisms, which will then self-fluoresce under ultraviolet light. This method requires fluorescence microscopy, which limits its use in small clinics.

Chamberland et al., "Chitinase-Gold Complex Used to Localize Chitin Ultrastructurally in Tomato Root Cells," Histochem. J., Vol. 17, pp 313–321 (1985), discusses the use of a fungal-extracted chitinase conjugated with gold to detect chitin in a *Fusarium oxysporum* infection of tomato root cells. Detection was performed with an electron microscope. Electron microscopy techniques are expensive, and would be impractical in many clinics and hospitals. This reference discusses only plants. Nothing in it suggests the use of a chitinase or other chitin-specific binding protein for the diagnosis of fungal or yeast infections in animal or human tissues or body fluids. See also Benhamou, et al., "Attempted Localization of a Substrate for Chitinases in Plant Cells Reveals Abundant N-acetyl-D-glucosamine Residues in Secondary Walls," Biology of the Cell, vol. 67, No. 3, pp. 341–50 (1989).

For the above reasons and others, there exists an unfulfilled need for an improved method of diagnosing fungal infections, especially in animals and humans, either in tissue samples or in body fluids.

SUMMARY

This invention provides a novel means of using a chitinase or other chitin-specific binding protein for diagnosing infections from fungal organisms, including yeasts, in animal and human tissues or body fluids. The novel method is simple, rapid, sensitive, quantitative, and general. A preferred chitinase, isolated and cloned from *Vibrio parahemolyticus* and designated "Chitinase VP1," binds so tightly to chitin that it (and an anti-chitinase antibody) can be used as a histochemical diagnostic probe with great sensitivity to specifically visualize fungal cell walls or yeast bud scars in tissue sections. A filter assay, enzyme-linked system will detect small amounts of fungal cell wall or yeast bud scar materials present in body fluids. The molecularly cloned Chitinase VP1 can be expressed and secreted in *E. coli* at a high level, producing about 30 mg/liter of culture medium.

DETAILED DESCRIPTION

The term "chitinase" generally describes an enzyme specific for the substrate chitin. Many different types of chitinases occur naturally. For example, chitinases are found in microbes such as Serratia, Vibrio, and Streptomyces. No commercial chitinase purified from a molecularly cloned gene has been previously available.

There are many glucosamine-containing, and N-acetyl-glucosamine-containing, compounds present in a typical animal species. Whether chitin, an N-acetyl-glucosamine-containing polymer, could be specifically identified by its corresponding enzyme from this background was not previously known or suggested. Furthermore, because the biological function of the chitinase enzymes is to degrade chitin, it is an unexpected result that a chitinase can bind to chitin tightly enough and for a long enough period of time, while surviving repeated washings, to serve as an effective stain, or a means of detecting chitin in animals. To the inventors' knowledge, no chitinase has previously been used to detect chitin or fungi (including yeasts) in an animal species or in humans.

This novel method will broadly detect a wide variety of fungal infections (including yeast infections), and may be used quantitatively. This test allows an early and definitive diagnosis of the etiologic fungal organisms causing opportunistic infections, so that implementation of an appropriate antifungal therapy can be initiated promptly. The assay recognizes yeasts by the chitin present in the yeast bud scars.

Chitin has not been previously reported as a natural substance in mammalian hosts. Natural chitin sources other than fungi include the exoskeletons of crustaceans and insects. These potential other sources of chitin should not significantly interfere with the use of this invention to identify fungal or yeast infections.

We have cloned the preferred Chitinase VP1 gene from *Vibrio parahemolyticus* into the pKK233 plasmid to create a new plasmid designated pKKA1, which was then transformed into *E. coli* strain JM101. The cloned Chitinase VP1 gene was expressed, and Chitinase VP1 was secreted efficiently into the medium. The enzyme was easily purified by ammonium sulfate precipitation. Its purity exceeded 90%, as determined by SDS-PAGE. The cloned Chitinase VP1 remained active within an unusually wide range of pH (pH 4.5–8.8), salt concentration (as high as 4M NaCl), and temperature (as high as 50° C.) Further details regarding the isolation, characterization, cloning, and sequencing of the novel Chitinase VP1 and its gene may be found in the following two draft manuscripts, neither of which is admitted to be prior art, and the entire disclosures of both of which are incorporated by reference: Ou et al., "Isolation, Characterization and Molecular Cloning of an Endo-Chitinase from *Vibrio parahemolyticus*," Louisiana State University draft manuscript (1991); and Lo et al., "DNA Sequence and High Expression Level for an Endo-Chitinase from Vibrio parahemolyticus," Louisiana State University draft manuscript (1991).

A sample of this transformed *E. coli* strain JM101 with the cloned Chitinase VP1 gene in plasmid pKKA1 was deposited with the American Type Culture Collection (ATCC), 12301 Parklawn Drive, Rockville, Md 20852 on Jan. 29, 1992, and was assigned ATCC Accession No. 68906. This deposit was made pursuant to a contract between ATCC and the assignee of this patent application, Board of Supervisors of Louisiana State University and Agricultural and Mechanical College. The contract with ATCC provides for permanent availability of the progeny of this *E. coli* strain to the public on the issuance of the U.S. patent describing and identifying the deposit or the publication or the laying open to the public of any U.S. or foreign patent application, whichever comes first, and for availability of the progeny of this *E. coli* strain to one determined by the U.S. Commissioner of Patents and Trademarks to be entitled thereto according to 35 U.S.C. § 122 and the Commissioner's rules pursuant thereto (including 37 C.F.R. §1.14, with particular reference to 886 OG 638). The assignee of the present application has agreed that if the *E. coli* strain on deposit should die or be lost or destroyed when cultivated under suitable conditions, it will be promptly replaced on notification with a viable culture of the same *E. coli* strain.

As used in the claims below, the term "Chitinase VP1" is intended to include not only exact duplicates of this enzyme, but also any enzyme having substantially the same amino acid sequence, and substantially the same chitin-binding activity.

With the use of a label conjugate complex, the presence of intact fungal organisms or fragments of chitinous cell walls can be quantified. It is expected that chitinases and other chitin-specific binding proteins, especially those conjugated to another enzyme to amplify the signal, will detect fragments of chitinous cell walls or yeast bud scars in circulation, even in cases where the fragments alone would not result in a viable culture for conventional organism isolation. The invasive biopsy required in many immunodepressed hosts for a proper diagnosis may be needed less often through the use of the filtration assay of body fluids in accordance with this invention.

Most fungi have chitin in their cell walls in at least some stage of their life cycles, or in yeast bud scars. A chitin-specific stain will therefore be chemically specific for fungi (including yeasts) (chitin being generally absent in bacteria and infectious protozoans), and will be broad spectrum. Fortunately, many current treatments for systemic fungal infections are broad-spectrum. A rapid, sensitive, and accurate diagnostic method that provides initial, early, and yet definitive diagnosis of disease-causing fungal organisms (perhaps without the need of a species-specific classification) will be more beneficial for patients (particularly AIDS patients), than other less sensitive or more time-consuming processes which aim at identifying species. Also, the course and efficacy of the antifungal treatment can readily be monitored. The quantitative capability of this method will also allow the development and optimization of treatment regimens through periodic monitoring of patient progress during treatment. Morphology of the fungal organisms delineated by a chitinase label generally provides sufficient information to identify the genus of the organisms. Species-specific identification, if needed, can be satisfied at a later opportune time using other conventional methods, such as blood cultures.

It may be the case that histological samples, smears, and other superficial samples from oral-esophageal fungal infections will have difficulty distinguishing between normal surface flora and disseminated deep infection. A large number of samples from this kind of infection, such as candidosis, will be needed to see whether a significant difference can be seen between samples from the Candida, and those of the normal mucosal flora.

The presence of chitin in etiologic agents of mycoses from animal and human tissue specimens will be verified either by a system of chitinase/rabbit polyclonal or monoclonal anti-chitinase/fluorescent goat anti-rabbit, or by chitinase directly coupled to fluorescein isothiocyanate (FITC). An enzyme-linked approach will use horseradish peroxidase directly coupled to chitinase, or an indirect antibody sandwich.

The high purity of the cloned Chitinase VP1 provided antigen for the production of a specific anti-chitinase polyclonal antibody in rabbit through techniques known in the art. The use of a monoclonal antibody in a probe was therefore unnecessary, although production of monoclonal antibodies through techniques known in the art is, of course, also possible. *Aspergillus niger* grown in bacteriologic media was successfully labelled using the cloned Chitinase VP1 and anti-Chitinase VP1 antibody with anti-rabbit IgG conjugated to FITC.

The system was tested in animal and human tissue sections with known fungal infections already identified by GMS or other tests. Tissue sections from animals with aspergillosis, cryptococcosis, and blastomycosis, as well as a tissue sample from a human AIDS patient with candidosis, were tested with the Chitinase VP1/ anti-Chitinase VP1 antibody probe, or with a Chitinase VP1-FITC direct conjugate probe, and examined. Aspergillus and blastomyces were positively identified in the presence of appropriate controls. *Cryptococcus neoformans*, which is frequently encapsulated with a thick polysaccharide, appeared to be labeled on a selective basis. In contrast to active organisms, most of the organisms with a thick polysaccharide capsule were poorly stained. Additional tests will determine if the selective staining is due to the lack of chitin in those cell walls, or to the inaccessibility of the probe due to the thick capsule.

Confirming the spectrum breadth of the chitinase diagnostic probe will require the identification of chitin in the fungal cell walls or yeast bud scars of the most common opportunistic fungi and true pathogenic fungi. The present invention can be used to verify the presence of chitin in these organisms prepared in thin sections. Chitinous fungi will be categorized separately from non-chitinous fungi, if any of the latter are found in this screening. It is expected that the accessibility of chitinase may in some cases be partially or totally blocked by the polysaccharide capsule in some fungi, such as that in Cryptococcus. Establishing the extent of this blockage will help to improve the proposed probe to overcome this obstacle. For example, proteases or polysaccharidases such as a glucanase or mannanase may be used as an adjuvant to uncover chitin in a complex cell wall, to facilitate chitinase accessibility. In addition, even in a single infection, Cryptococci can vary in their biochemical components. Thus at least some Cryptococci should be accessible to this diagnostic method at any given time.

Opportunistic fungal organisms are generally nonpathogenic in hosts with healthy immune systems. A variety of opportunistic fungal organisms will be tested, including those most commonly found in AIDS patients. The cells will be fixed with either methanol or 4% paraformaldehyde. The specimen will be embedded in paraffin and thin sectioned. After a series of standard deparaffination procedures with xylene and a series of ethanol solutions at different concentrations, Chitinase VP1 (100 µl of 1.0 mg/ml) and diluted anti-Chitinase VP1 (100 µl) as well as the labeling probe will be applied to the BSA-pretreated specimens. The specimen will be washed with phosphate-buffered saline between additions of reagents. Endogenous peroxidase in the specimen will be removed if peroxidase conjugate is used as the labeling probe. Several labeling probes will be investigated, to determine the best such label for these tests. The efficacy of Protein A-Peroxidase or Protein A-FITC conjugate, anti-rabbit IgG-Peroxidase or FITC conjugate, Peroxidase-antiperoxidase complex and avidin-biotin will be evaluated. The specimen will be mounted in proper medium for observations. It may be possible to label the chitinase directly with various reagents, to eliminate the need for an anti-chitinase antibody. A direct conjugate of Chitinase VP1 with FITC or horseradish peroxidase has been studied, and has shown good results. Whether the chitin-specific binding protein or its antibody is labelled, detectable labels which may be used include a radioactive material, a fluorophore, a dye, an electron-dense compound, and an enzyme. This variety of potential labels broadens the possible applications of this invention. A GMS stain will be used in parallel for comparison. If organisms prepared in thin sections are successfully labeled with the proposed probe, it is believed that the same observation should be seen in a variety of actual pathologic specimens, as has already been seen in Blastomyces, Aspergillus, Cryptococcus, and Candida, as previously discussed.

Positive results in testing the chitinous materials in suspension show that this system should also work in testing body fluid samples. A small filter unit (Spin-X, CoStar Co.) equipped with polyvinylidene difluoride (PVDF, Immobilon, Millipore, USA) membrane which had been pretreated with bovine serum albumin (BSA) was used to retain chitinous materials, specifically swollen chitin in suspension. Other reagents in the diagnostic probe were applied in the following order: Chitinase VP1, anti-chitinase VP1 antibody, and Protein A-Peroxidase conjugate. (The use of enzyme in place of FITC allows quantitative analysis.) After addition of a chromogenic developing solution (4-chloro-N-naphthol and $H_2O_2$), only the unit with chitin, chitinase, and anti-chitinase was positive. It should be feasible to retain chitinous fungal organisms, or their chitinous cell wall or yeast bud scar materials, on the membrane without interference by other proteins present in body fluids. Subsequently, the retained chitinous materials can be qualitated by the diagnostic probe: chitinase (with or without anti-chitinase antibody), and a chromogenie label conjugate. Formaldehyde-fixed Aspergillus labeled with the Chitinase VP 1-peroxidase direct conjugate indicated that mycelial fragments and cells can be trapped on the filters for direct catalytic chromogenic assay. On the other hand, cellulose and glucans stuck to the membranes did not bind chitinase.

The following method will be used to demonstrate further the feasibility of this technique for diagnosis in body fluids. A set of fungal organisms will be grown in suspension. The cells will be mixed with normal human serum, and processed using a small filter unit as the retention matrix. The smallest number of fungal organisms or the smallest amount of fungal cell wall or yeast bud scar materials in 100 μl of serum giving a definitive result will be determined. The contaminated serum will be diluted for easy filtration, and the prospective fungal organisms or fragments of the cell walls or bud scars trapped by the membrane will be fixed with either methanol or paraformaldehyde. The filter will be washed twice with distilled water to lyse red blood cells when dealing with actual specimens, and then washed three times with phosphate-buffered saline plus 0.05% Tween 20, followed by the addition of 100 μl of cloned Chitinase VP1 (1.0 mg/ml) for 20 min at room temperature. (Digestion at a higher temperature will also be attempted. ) After washing the filter with phosphate-buffered saline, diluted anti-Chitinase VP1 antibody (100 μl) will be added to the filter and incubated for 30 min at room temperature. A labeling probe will be subsequently added to the filter after washing. Quantitative analysis can be achieved by using an appropriate labeling probe. If peroxidase is used in conjugation, a soluble chromogenic developing solution with ABTS can be used for quantitative analysis. Direct conjugates of Chitinase VP1 will also be used in this study. To test that the system is specific for fungal organisms, several control groups will be tested as well. These control groups will include serum contaminated with other known bacteria, viruses, or protozoa.

As an example, fragments of Aspergillus cell wall, mycelial fragments obtained by sonication, and whole cells will be suspended, and the suspensions diluted ten or more times. Each resulting solution will be filtered through a 10,000 molecular weight cut-off filter. Chitinase VP1, anti-Chitinase VP1 antibody, and horseradish peroxidase-labelled goat anti-rabbit IgG will be applied to the filters (a direct conjugate will also be used), and the catalytic potential of the bound enzyme will be assayed to determine the sensitivity of the assay for cell wall fragments in body fluids. Mycelial fragments of Aspergillus have been successfully tested in this system.

It has previously been the case that certain deep invasive fungal infections could only be properly diagnosed by histologic examination. It is possible that other fungal antigens or whole cells may substantially disappear from circulation during certain stages of the disease. It is still desirable and safer, if possible, to obtain a definitive diagnosis by testing body fluids, rather than by examining histologic specimens. Comparisons will therefore be made between the effectiveness of Chitinase VP1 as a diagnostic probe in samples of body fluids, with results from other diagnostic methods in present use (including histologic identification if necessary).

Specimens collected from animals will be processed appropriately for histologic identification by embedding and thin sectioning before specific staining procedures. Also, fluid samples will be processed for in vitro testing in the small filter unit using Chitinase VP1 as the diagnostic probe. The procedures will be generally as described above. Correlation with other diagnostic procedures will be evaluated in a blind study with several control groups. Specimens from animals with non-fungal infections, bacteremia, virus infection, and other disorders uncomplicated by fungal infections will also be tested as controls. Later, similar tests will be conducted with specimens from human patients, including AIDS patients.

It will also be appreciated by those of skill in the art that certain other chitin-specific binding proteins can be used in place of a chitinase, without departing from the spirit of the invention. An example of such a protein is the chitin-adhesion protein of *Vibrio furnissii*; see Yu et al., J. Biol.

Chem., vol. 266, pp 24260–24267 (1991) (not admitted to prior art), the entire disclosure of which is incorporated by reference.

Although Chitinase VP1 was the only chitinase which had been successfully tested in the process of this invention at the time this application was filed, it is expected that other substantially pure chitinases or other substantially pure chitin-specific binding proteins will work as well. Determining whether a particular other chitinase or chitin-specific binding protein will work in this invention is well within the skill of the ordinary worker in the art, following the experimental guidelines given above. As used in the claims below, a "substantially pure" chitinase or chitin-specific binding protein is one in which any contaminants which may be present are in sufficiently low concentrations as to avoid significant interference with the specificity and selectivity of the chitin-binding reaction in diagnosing the presence of chitin or fungi (including yeasts) in a sample; in other words, the concentrations of any contaminants in a "substantially pure" chitinase or chitin-specific binding protein do not significantly affect the frequency of false positive or false negative results. By way of example, the cloned Chitinase VP1, isolated at 90% purity as described above, is considered to be "substantially pure."

We claim:

1. A method for detecting chitin in a sample comprising a human or animal tissue, or comprising a human or animal body fluid, said method comprising the steps of:
   (a) contacting the sample with a substance comprising Chitinase VP1; and
   (b) analyzing the sample for the presence of Chitinase VP1 bound to chitin.

2. A method as recited in claim 1, wherein said Chitinase VP1 is conjugated to a detectable label.

3. A method as recited in claim 2, wherein the detectable label is selected from the group consisting of radioactive material, fluorophore, dye, an electron-dense compound, and an enzyme.

4. A method as recited in claim 2, wherein the sample comprises an animal tissue or a human tissue.

5. A method as recited in claim 4, wherein said analyzing step comprises analyzing the sample for the presence of Chitinase VP1 bound to chitin in fungal cell walls.

6. A method as recited in claim 4, wherein said analyzing step comprises analyzing the sample for the presence of Chitinase VP1 bound to chitin in yeast bud scars.

7. A method as recited in claim 2, wherein the sample comprises an animal body fluid or a human body fluid.

8. A method as recited in claim 7, wherein said analyzing step comprises analyzing the sample for the presence of Chitinase VP1 bound to chitin in fungal cell walls.

9. A method as recited in claim 7, wherein said analyzing step comprises analyzing the sample for the presence of Chitinase VP1 bound to chitin in yeast bud scars.

10. A method as recited in claim 1, additionally comprising the step of contacting the sample with at least one reagent comprising an antibody to Chitinase VP1.

11. A method as recited in claim 10, wherein at least one said reagent is conjugated to a detectable label.

12. A method as recited in claim 11, wherein the detectable label is selected from the group consisting of radioactive material, fluorophore, dye, an electron-dense compound, and an enzyme.

13. A method as recited in claim 11, wherein the sample comprises an animal tissue or a human tissue.

14. A method as recited in claim 13, wherein said analyzing step comprises analyzing the sample for the presence of Chitinase VP1 bound to chitin in fungal cell walls.

15. A method as recited in claim 13, wherein said analyzing step comprises analyzing the sample for the presence of Chitinase VP1 bound to chitin in yeast bud scars.

16. A method as recited in claim 11, wherein the sample comprises an animal body fluid or a human body fluid.

17. A method as recited in claim 12, wherein said analyzing step comprises analyzing the sample for the presence of Chitinase VP1 bound to chitin in fungal cell walls.

18. A method as recited in claim 16, wherein said analyzing step comprises analyzing the sample for the presence of Chitinase VP1 bound to chitin in yeast bud scars.

19. A method for detecting chitin in a sample comprising a human or animal tissue, or comprising a human or animal body fluid, said method comprising the steps of:
   (a) contacting the sample with a substance comprising a substantially pure chitinase; and
   (b) analyzing the sample for the presence of the chitinase bound to chitin.

20. A method as recited in claim 19, wherein said chitinase is conjugated to a detectable label.

21. A method as recited in claim 20, wherein the detectable label is selected from the group consisting of radioactive material, fluorophre, dye, an electron-dense compound, and an enzyme.

22. A method as recited in claim 20, wherein the sample comprises an animal tissue or a human tissue.

23. A method as recited in claim 22, wherein said analyzing step comprises analyzing the sample for the presence of the chitinase bound to chitin in fungal cell walls.

24. A method as recited in claim 22, wherein said analyzing step comprises analyzing the sample for the presence of the chitinase bound to chitin in yeast bud scars.

25. A method as recited in claim 20, wherein the sample comprises an animal body fluid or a human body fluid.

26. A method as recited in claim 25, wherein said analyzing step comprises analyzing the sample for the presence of the chitinase bound to chitin in fungal cell walls.

27. A method as recited in claim 25, wherein said analyzing step comprises analyzing the sample for the presence of the chitinase bound to chitin in yeast bud scars.

28. A method as recited in claim 19, additionally comprising the step of contacting the sample with at least one reagent comprising an antibody to said chitinase.

29. A method as recited in claim 28, wherein at least one said reagent is conjugated to a detectable label.

30. A method as recited in claim 29, wherein the detectable label is selected from the group consisting of radioactive material, fluorophore, dye, an electron-dense compound, and an enzyme.

31. A method as recited in claim 29, wherein the sample comprises an animal tissue or a human tissue.

32. A method as recited in claim 31, wherein said analyzing step comprises analyzing the sample for the presence of the chitinase bound to chitin in fungal cell walls.

33. A method as recited in claim 31, wherein said analyzing step comprises analyzing the sample for the presence of the chitinase bound to chitin in yeast bud scars.

34. A method as recited in claim 29, wherein the sample comprises an animal body fluid or a human body fluid.

35. A method as recited in claim 34, wherein said analyzing step comprises analyzing the sample for the presence of the chitinase bound to chitin in fungal cell walls.

36. A method as recited in claim 34, wherein said analyzing step comprises analyzing the sample for the presence of the chitinase bound to chitin in yeast bud scars.

* * * * *